United States Patent
Nageshwar

(10) Patent No.: US 10,130,275 B2
(45) Date of Patent: Nov. 20, 2018

(54) METHOD AND APPARATUS FOR AUTONOMIC NERVOUS SYSTEM SENSITIVITY-POINT TESTING

(71) Applicant: DyAnsys, Inc., San Mateo, CA (US)

(72) Inventor: Srini Nageshwar, Los Gatos, CA (US)

(73) Assignee: DYANSYS, INC., San Mateo, CA (US)

( * ) Notice: Subject to any disclaimer, the term of this patent is extended or adjusted under 35 U.S.C. 154(b) by 30 days.

(21) Appl. No.: 13/916,944

(22) Filed: Jun. 13, 2013

(65) Prior Publication Data
US 2014/0371621 A1    Dec. 18, 2014

(51) Int. Cl.
*A61B 5/04* (2006.01)
*A61B 5/00* (2006.01)
*A61B 5/053* (2006.01)

(52) U.S. Cl.
CPC ........ *A61B 5/04001* (2013.01); *A61B 5/0002* (2013.01); *A61B 5/0533* (2013.01); *A61B 5/4035* (2013.01)

(58) Field of Classification Search
None
See application file for complete search history.

(56) References Cited

U.S. PATENT DOCUMENTS

| | | | |
|---|---|---|---|
| 524,660 A | 8/1894 | Woodward | |
| 3,646,606 A * | 2/1972 | Buxton | A61B 5/0006 128/903 |
| 3,872,252 A * | 3/1975 | Malchman | A61B 5/0006 128/904 |
| 3,939,841 A | 2/1976 | Dohring et al. | |
| 4,244,375 A | 1/1981 | Farrar et al. | |
| 4,262,672 A | 4/1981 | Kief | |
| 4,428,380 A * | 1/1984 | Wong | A61B 5/0404 600/513 |
| 4,677,984 A * | 7/1987 | Sramek | A61B 5/0456 600/492 |
| 4,685,466 A | 8/1987 | Rau | |
| 4,784,162 A * | 11/1988 | Ricks | A61B 5/0002 600/484 |
| 5,012,816 A | 5/1991 | Lederer | |
| 5,058,605 A | 10/1991 | Slovak | |

(Continued)

FOREIGN PATENT DOCUMENTS

| | | |
|---|---|---|
| AT | 150525 | 4/1937 |
| CH | 239028 | 9/1945 |

(Continued)

OTHER PUBLICATIONS

International Search Report for PCT application PCT/US2013/045668 (dated Sep. 27, 2013).

(Continued)

*Primary Examiner* — Matthew Kremer
(74) *Attorney, Agent, or Firm* — Alston & Bird LLP

(57) ABSTRACT

A method for autonomic nervous system sensitivity-point testing on a skin of a patient is described. The method includes generating an electrotherapy signal that stimulates a vagal response of an autonomic nervous system of the patient when the patient is tested. The method further includes providing an electrically conductive tip that electrically contacts but does not puncture the skin when the patient is tested and coupling the electrotherapy signal to the electrically conductive tip.

51 Claims, 4 Drawing Sheets

(56) References Cited

U.S. PATENT DOCUMENTS

| | | | | |
|---|---|---|---|---|
| 5,269,302 | A | * | 12/1993 | Swartz .................... A61N 1/38 607/45 |
| 5,285,793 | A | | 2/1994 | Slovut et al. |
| 5,324,287 | A | | 6/1994 | Szeles |
| 5,349,962 | A | | 9/1994 | Lockard et al. |
| 5,449,378 | A | | 9/1995 | Schouenborg |
| 5,578,065 | A | | 11/1996 | Hattori et al. |
| 5,645,070 | A | | 7/1997 | Turcott |
| 5,772,688 | A | | 6/1998 | Muroki |
| 5,823,788 | A | | 10/1998 | Lemelson et al. |
| 5,957,862 | A | | 9/1999 | Lu et al. |
| 5,957,951 | A | | 9/1999 | Cazaux et al. |
| 5,971,922 | A | | 10/1999 | Arita et al. |
| 6,117,075 | A | | 9/2000 | Barnea |
| 6,445,955 | B1 | | 9/2002 | Michelson et al. |
| 6,493,592 | B1 | | 12/2002 | Leonard et al. |
| 6,539,264 | B1 | | 3/2003 | Bishay et al. |
| 6,735,471 | B2 | * | 5/2004 | Hill et al. ....................... 607/2 |
| 6,999,445 | B1 | | 2/2006 | Dmitriev et al. |
| 7,092,849 | B2 | | 8/2006 | Lafitte et al. |
| 7,336,993 | B1 | | 2/2008 | Szeles |
| 7,660,637 | B2 | | 2/2010 | Szeles |
| 7,797,041 | B2 | | 9/2010 | Libbus et al. |
| 8,868,199 | B2 | | 10/2014 | Kaula et al. |
| 2002/0013613 | A1 | | 1/2002 | Hailer et al. |
| 2002/0077560 | A1 | | 6/2002 | Kramer et al. |
| 2003/0236469 | A1 | | 12/2003 | Hedgecock |
| 2004/0210261 | A1 | | 10/2004 | King et al. |
| 2006/0064139 | A1 | | 3/2006 | Chung et al. |
| 2006/0074337 | A1 | | 4/2006 | Yoo et al. |
| 2006/0122675 | A1 | * | 6/2006 | Libbus et al. ............... 607/116 |
| 2006/0195164 | A1 | * | 8/2006 | Sondergaard et al. ......... 607/76 |
| 2006/0202805 | A1 | * | 9/2006 | Schulman et al. ......... 340/10.41 |
| 2007/0179816 | A1 | | 8/2007 | Lemme et al. |
| 2007/0219455 | A1 | | 9/2007 | Wong et al. |
| 2007/0239210 | A1 | * | 10/2007 | Libbus et al. ..................... 607/2 |
| 2008/0071188 | A1 | | 3/2008 | Home et al. |
| 2008/0249439 | A1 | * | 10/2008 | Tracey et al. .................. 601/46 |
| 2008/0262376 | A1 | | 10/2008 | Price |
| 2008/0275468 | A1 | | 11/2008 | Chuang et al. |
| 2008/0288016 | A1 | * | 11/2008 | Amurthur et al. .............. 607/44 |
| 2009/0105605 | A1 | | 4/2009 | Abreu |
| 2009/0171420 | A1 | | 7/2009 | Brown et al. |
| 2009/0181353 | A1 | | 7/2009 | Dasgupta et al. |
| 2009/0292180 | A1 | | 11/2009 | Mirow et al. |
| 2009/0326595 | A1 | | 12/2009 | Brockway et al. |
| 2010/0168822 | A1 | | 7/2010 | Szeles |
| 2010/0198142 | A1 | * | 8/2010 | Sloan et al. .................... 604/66 |
| 2010/0286734 | A1 | | 11/2010 | Yun et al. |
| 2011/0007950 | A1 | * | 1/2011 | Deutsch ....................... 382/111 |
| 2011/0028860 | A1 | * | 2/2011 | Chenaux et al. .............. 600/554 |
| 2011/0071418 | A1 | | 3/2011 | Stellar et al. |
| 2011/0167103 | A1 | | 7/2011 | Acosta et al. |
| 2011/0238083 | A1 | * | 9/2011 | Moll et al. ..................... 606/130 |
| 2011/0319966 | A1 | | 12/2011 | Sadkhin |
| 2012/0053648 | A1 | | 3/2012 | Neher et al. |
| 2012/0075464 | A1 | * | 3/2012 | Derenne et al. .............. 348/135 |
| 2012/0101358 | A1 | | 4/2012 | Boettcher et al. |
| 2012/0226333 | A1 | | 9/2012 | Szeles |
| 2012/0277833 | A1 | | 11/2012 | Gerber et al. |
| 2013/0093829 | A1 | | 4/2013 | Rosenblatt et al. |
| 2013/0096641 | A1 | | 4/2013 | Strother et al. |
| 2013/0117669 | A1 | | 5/2013 | Shikhman et al. |
| 2014/0370476 | A1 | | 12/2014 | Nageshwar |
| 2014/0371608 | A1 | | 12/2014 | Nageshwar |
| 2014/0371621 | A1 | | 12/2014 | Nageshwar |
| 2014/0371820 | A1 | | 12/2014 | Nageshwar |
| 2016/0113526 | A1 | | 4/2016 | Nageshwar et al. |
| 2017/0143247 | A1 | | 5/2017 | Nageshwar |

FOREIGN PATENT DOCUMENTS

| | | |
|---|---|---|
| CH | 620821 | 12/1980 |
| CN | 1788265 A | 6/2006 |
| DE | 319602 | 9/1914 |
| DE | 29720785 | 2/1998 |
| EP | 0229200 | 7/1987 |
| EP | 0759307 | 2/1997 |
| FR | 969374 | 12/1950 |
| FR | 1297117 | 5/1962 |
| FR | 2345994 | 10/1977 |
| FR | 2354759 | 1/1978 |
| GB | 1514079 | 6/1978 |
| GB | 1603726 | 11/1981 |
| GB | 2115700 | 9/1983 |
| JP | 04-314459 | 11/1992 |
| SU | 957917 | 9/1982 |
| SU | 1296164 | 3/1987 |
| WO | WO 2000/074331 | 12/2000 |
| WO | WO 2005/001706 | 1/2005 |
| WO | WO2010/014259 | 2/2010 |
| WO | WO 2012/078924 A1 | 6/2012 |
| WO | WO 2014/200488 A1 | 12/2014 |
| WO | WO 2014/200489 A2 | 12/2014 |
| WO | WO 2014/200492 A1 | 12/2014 |
| WO | WO 2014/200498 A1 | 12/2014 |

OTHER PUBLICATIONS

Non-Final Office Action for U.S. Appl. No. 13/916,934 dated Sep. 23, 2014, 12 pages.
Non-Final Office Action for U.S. Appl. No. 13/917,471 dated Sep. 22, 2014, 11 pages.
International Search Report for PCT application PCT/US2013/045587 (dated Jun. 13, 2013).
Lafitte et al. "Towards assessing the sympathovagal balance," Medical and Biological Engineering and Computing vol. 44, Issue 8, pp. 675-682 (Aug. 2006).
Schondorf et al. "Sympathovagal Balance," Poster #44 23rd International Symposium on the Autonomic Nervous System Atlantis Resort, Paradise Island, Bahamas (Nov. 2012).
Final Office Action for U.S. Appl. No. 13/916,934 dated Mar. 3, 2015, 9 pages.
Final Office Action for U.S. Appl. No. 13/917,471 dated Feb. 20, 2015, 11 pages.
International Search Report for PCT application PCT/US2013/045588 (dated Jan. 10, 2014).
International Search Report for PCT application PCT/US2013/045712 (dated Apr. 9, 2014).
Abarbanel, H.D.I, "The analysis of observed chaotic data in physical systems," Reviews of Modern Physics, American Physical Society, 65(4):1331-1392, (1993).
Morfill et al., "Komplexitatsanalyse in der Kardiologie," Physikalische Blater, 50(2):156-160, (1994).
U.S. Appl. No. 10/961,710, Non-Final Office Action dated Dec. 2, 2005.
U.S. Appl. No. 10/961,710, Notice of Allowance dated Apr. 17, 2006.
U.S. Appl. No. 13/916,934, Advisory Action dated May 14, 2015.
U.S. Appl. No. 13/916,934, Final Office Action dated Apr. 13, 2016.
U.S. Appl. No. 13/916,934, Non-Final Office Action dated Aug. 20, 2015.
U.S. Appl. No. 13/916,975, Non-Final Office Action dated Jun. 2, 2015.
U.S. Appl. No. 13/917,471, Advisory Action dated May 10, 2016.
U.S. Appl. No. 13/917,471, Final Office Action dated Feb. 26, 2016.
U.S. Appl. No. 13/917,471, Non-Final Office Action dated Aug. 12, 2015.
U.S. Appl. No. 13/916,934, Advisory Action dated Oct. 26, 2016.
U.S. Appl. No. 13/916,975, Final Office Action dated Aug. 4, 2016.
WIPO Application No. PCT/IB2003/002522, PCT International Search Report dated Feb. 9, 2004.
WIPO Application No. PCT/US2013/045587, PCT International Preliminary Report on Patentability dated Dec. 15, 2015.
WIPO Application No. PCT/US2013/045587, PCT Written Opinion of the International Searching Authority dated Sep. 19, 2013.
WIPO Application No. PCT/US2013/045588, PCT International Preliminary Report on Patentability dated Dec. 15, 2015.

(56) References Cited

OTHER PUBLICATIONS

WIPO Application No. PCT/US2013/045588, PCT Written Opinion of the International Searching Authority dated Jan. 10, 2014.
WIPO Application No. PCT/US2013/045668, PCT International Preliminary Report on Patentability dated Dec. 15, 2015.
WIPO Application No. PCT/US2013/045668, PCT Written Opinion of the International Searching Authority dated Sep. 27, 2013.
WIPO Application No. PCT/US2013/045712, PCT International Preliminary Report on Patentability dated Dec. 15, 2015.
WIPO Application No. PCT/US2013/045712, PCT Written Opinion of the International Searching Authority dated Apr. 9, 2014.
EPO Application No. EP13886872, Supplementary European Search Report dated May 30, 2017.
EPO Application No. EP13887010, Supplemental European Search Report dated May 30, 2017.
EPO Application No. EP13886840, Supplementary European Search Report dated Feb. 3, 2017.
EPO Application No. EP13886698, Supplementary European Search Report dated Mar. 20, 2017.
U.S. Appl. No. 13/916,934, Final Office Action dated Nov. 2, 2017.
U.S. Appl. No. 13/916,934, Non-Final Office Action dated Apr. 20, 2017.

* cited by examiner

METHOD AND APPARATUS FOR AUTONOMIC NERVOUS SYSTEM SENSITIVITY-POINT TESTING

CROSS-REFERENCES TO RELATED APPLICATIONS

This application is related to U.S. Pat. No. 7,092,849, titled "EXTRACTING CAUSAL INFORMATION FROM A CHAOTIC TIME SERIES," granted Aug. 15, 2006, the content of which is incorporated herein by reference in its entirety. This application is also related to the following applications filed herewith: U.S. patent application Ser. No. 13/917,417, titled "STIMULATIVE ELECTROTHERAPY USING AUTONOMIC NERVOUS SYSTEM CONTROL," U.S. patent application Ser. No. 13/916,975, titled "COMPUTER-IMPLEMENTED TRAINING OF A PROCEDURE," and U.S. patent application Ser. No. 13/916,934, titled "METHOD AND APPARATUS FOR STIMULATIVE ELECTROTHERAPY," the contents of all of which are incorporated herein by reference in their entirety.

BACKGROUND

The present invention relates generally to a method and apparatus for testing a patient's skin, and in particular, to testing a patient's skin to find autonomic nervous system sensitivity-points.

Measures of heart rate variability have been shown to be a powerful means of assessing the influence of the autonomic nervous system on the cardiac system. Indeed, the autonomic nervous system, with its sympathetic and parasympathetic, hereinafter also referred to as "vagal" subsystems, governs involuntary actions of the cardiac muscle and every visceral organ in the body.

The autonomic nervous system is not directly accessible to voluntary control. Instead, it operates in an autonomic fashion on the basis of autonomic reflexes and central control. One of its major functions is the maintenance of homeostasis within the body. The autonomic nervous system further plays an adaptive role in the interaction of the organism with its surroundings.

In many diseases, the sympathetic and/or parasympathetic parts of the autonomic nervous system are affected leading to autonomic dysfunction. It is then important to have reliable and representative measures of the activity and the state of the autonomic nervous system.

U.S. Pat. No. 7,092,849 to Lafitte, et al. describes a method, a system, and a computer code for analyzing the state of the autonomic nervous system from a time-varying signal representing a chaotic series of time intervals between quasi-periodical events produced by the cardiac system governed by the autonomic system. Thus, real-time monitoring of the sympathovagal balance between the parasympathetic and the sympathetic components of the autonomic nervous system is possible.

The autonomic nervous system plays an important role in pain modulation and perception and chronic pain is likely due to a malfunction in the body's central nervous system. While there are many medications and physical therapies that are used to treat pain, they do not cure it and only mask the pain response, sometimes with undesired side effects such as with narcotic medications.

A point stimulation device is a non-narcotic combination of permanent acupuncture-like needles and electrical stimulation used to treat chronic pain over time. A point stimulation device uses auricular acupuncture as a treatment based on normalizing the body's dysfunction through stimulation of points on the ear. The resulting amelioration of pain and illness is believed to be through the reticular formation and the sympathetic and parasympathetic nervous systems. Specific points in the ear are related to major organs in the body. However, existing medical devices and treatment protocols for testing and locating sensitivity-points on the skin surface for point stimulation needle insertion have not taken advantage of the capabilities of real-time sympathovagal balance monitoring.

BRIEF SUMMARY

According to one embodiment of the present invention, a method for autonomic nervous system sensitivity-point testing on a skin of a patient is described. The method includes generating an electrotherapy signal that stimulates a vagal response of an autonomic nervous system of the patient when the patient is tested. The method further includes providing an electrically conductive tip that electrically contacts but does not puncture the skin when the patient is tested and coupling the electrotherapy signal to the electrically conductive tip.

According to one embodiment, generating the electrotherapy signal includes wirelessly setting a characteristic of the electrotherapy signal. According to one embodiment, the characteristic is selected from the group consisting of a frequency, an amplitude, a pulse shape, and a duty cycle. According to one embodiment, the method further includes generating an electrical resistance-measuring signal, and coupling the electrical resistance-measuring signal to the electrically conductive tip.

According to one embodiment, the method further includes choosing a first portion of skin of the patient, applying the electrotherapy signal to the first portion of skin with the electrically conductive tip, measuring a first sympathovagal balance of the patient, and determining a response outcome based on the first sympathovagal balance. The response outcome is positive when the first sympathovagal balance moves towards the vagal response. The response outcome is negative when the first sympathovagal balance does not move towards the vagal response.

According to one embodiment, the method further includes choosing a second portion of skin of the patient abutting the first portion of skin when the response outcome is negative. The method further includes repeating applying the electrotherapy signal, measuring the first sympathovagal balance, and determining the response outcome until the response outcome is positive or until a first predetermined number of portions of skin are tested.

According to one embodiment, choosing a first portion of skin includes obtaining a preliminary location of the first portion of skin from a graphical user interface coupled to a computer executing a program responsive to a symptom of the patient. According to one embodiment, the first portion of skin is located on an ear of the patient.

According to one embodiment, applying the electrotherapy signal includes applying an electrode to a second portion of the skin. The electrode is a return signal path for the electrotherapy signal thereby enabling a gloved medical practitioner to facilitate applying the electrotherapy signal.

According to one embodiment, measuring a first sympathovagal balance includes coupling an autonomic nervous system monitor to the patient, and analyzing the state of the autonomic nervous system of the patient from a time-varying signal representing a chaotic series of time intervals between quasi-periodical events produced by a cardiac system of the patient. According to one embodiment, the method further includes inserting an electrotherapy needle at the first portion of skin when the response outcome is positive.

According to one embodiment, the method further includes measuring a second sympathovagal balance of the patient, and determining a reversal outcome based on the second sympathovagal balance. The reversal outcome is positive when the second sympathovagal balance reverses from a sympathetic response towards a vagal response. The reversal outcome is negative when the second sympathovagal balance does not reverse from a sympathetic response towards a vagal response.

According to one embodiment, the method further includes removing the electrotherapy needle from the first portion of the skin when the reversal outcome is negative, and choosing a second portion of the skin of the patient abutting the first portion of the skin. The method further includes repeating inserting, measuring the second sympathovagal balance, and determining the reversal outcome until the reversal outcome is positive or until a second predetermined number of portions of skin are tested.

According to one embodiment, the method further includes determining a number of inserted electrotherapy needles when the reversal outcome is positive, and finishing the testing when the number of inserted electrotherapy needles is equal to a predetermined number of electrotherapy needles. The method further includes repeating choosing, applying the electrotherapy signal, measuring the first sympathovagal balance, determining the response outcome, inserting, measuring the second sympathovagal balance, and determining the reversal outcome when the number of inserted electrotherapy needles is less than the predetermined number of electrotherapy needles. According to one embodiment, the predetermined number of electrotherapy needles is equal to three.

According to one embodiment, choosing the first portion of skin includes generating an electrical resistance-measuring signal, coupling the electrical resistance-measuring signal to the electrically conductive tip, and applying the electrical resistance-measuring signal to the first portion of skin with the electrically conductive tip. The method further includes measuring the electrical resistance at the first portion of skin, providing an indication responsive to a value of the electrical resistance, and moving the electrically conductive tip in response to the indication to selectively find a low resistance location of skin near the first portion of skin.

According to one embodiment, applying the resistance-measuring signal includes applying an electrode to a second portion of skin. The electrode is a return signal path for the resistance-measuring signal thereby enabling a gloved medical practitioner to facilitate applying the electrical resistance-measuring signal. According to one embodiment, applying the electrotherapy signal includes switching the electrical probe from a resistance-measuring mode to an autonomic nervous system mode.

According to one embodiment of the present invention, an electrical apparatus for autonomic nervous system sensitivity-point testing on a skin of a patient is described. The electrical apparatus includes a circuit adapted to generate an electrotherapy signal that stimulates a vagal response of an autonomic nervous system of the patient when the patient is tested, and an electrically conductive tip adapted to electrically contact but not puncture the skin when the patient is tested. The electrotherapy signal is coupled to the electrically conductive tip.

According to one embodiment, the electrical apparatus further includes an electrode adapted to be applied to a second portion of skin. The electrode is a return signal path for the electrotherapy signal thereby enabling a gloved medical practitioner to facilitate applying the electrotherapy signal to the patient.

According to one embodiment, the circuit includes a wireless radio transceiver, and a control circuit adapted to set a characteristic of the electrotherapy signal received by the wireless transceiver. According to one embodiment, the wireless radio transceiver operates on a transmission standard selected from Bluetooth®, 6LoWPAN®, ZigBee®, DASH7®, Z-Wave®, MiWi®, or OSION®.

According to one embodiment, the circuit is further adapted to generate an electrical resistance-measuring signal. The electrical resistance-measuring signal is coupled to the electrically conductive tip responsive to a switch position that selectively couples the electrotherapy signal or the electrical resistance-measuring signal to the electrically conductive tip. According to one embodiment, the electrical apparatus further includes an electrode adapted to be applied to a second portion of skin. The electrode is a return signal path for the electrical resistance-measuring signal thereby enabling a gloved medical practitioner to facilitate applying the electrical resistance-measuring signal to the patient.

According to one embodiment, the electrical apparatus further includes an indicator responsive to a value of electrical resistance measured by the circuit. According to one embodiment, the indicator is a visual indicator, a sonic indicator, or a vibrational indicator.

According to one embodiment of the present invention, an electrical testing apparatus includes a battery, a circuit adapted to generate a periodic signal in time, and an electrically conductive tip adapted to electrically contact but not puncture a first portion of a surface when the surface is tested. The periodic signal is coupled to the electrically conductive tip.

According to one embodiment, the electrical testing apparatus further includes an electrode adapted to be applied to a second portion of the surface. The electrode is a return signal path for the periodic signal thereby enabling a gloved tester to facilitate applying the periodic signal to the first portion of the surface when the surface is tested.

According to one embodiment, the electrical testing apparatus further includes a housing having an insulating surface and at least a first orifice in the insulating surface. The electrically conductive tip is adapted to protrude outside the housing through the first orifice. The housing encloses the battery and the circuit. The housing has a shape that is adapted to be hand held when the surface is tested. According to one embodiment, the housing is adapted to hermetically seal the electrical testing apparatus.

According to one embodiment, the electrical testing apparatus further includes an electrode adapted to be applied to a second portion of the surface. The electrode is a return signal path for the electrical resistance-measuring signal thereby enabling a gloved tester to facilitate applying the electrical resistance-measuring signal to the surface when the surface is tested.

According to one embodiment of the present invention, a method for electrical testing includes providing a battery, and generating a periodic signal in time from a circuit. The method for electrical testing further includes providing an electrically conductive tip adapted to electrically contact but not puncture a first portion of a surface when the surface is tested, and coupling the periodic signal to the electrically conductive tip.

According to one embodiment, the method further includes providing a housing having an insulating surface and at least a first orifice in the insulating surface. The method further includes protruding the electrically conductive tip outside the housing through the first orifice, enclosing the battery and the circuit with the housing, and shaping the housing to be hand held when the surface is tested. According to one embodiment, the method further comprises hermetically sealing the electrical testing apparatus with the housing.

According to one embodiment, the method further includes applying an electrode to a second portion of the surface, the electrode being a return signal path for the periodic signal. The method further includes enabling a gloved tester to facilitate applying the periodic signal to the first portion of the surface when the surface is tested. According to one embodiment, the method further includes providing a wireless radio transceiver, setting a characteristic of the periodic signal via a control circuit, and receiving the characteristic by an input of the wireless transceiver.

According to one embodiment, the method further includes generating an electrical resistance-measuring signal by the circuit. The method further includes coupling the electrical resistance-measuring signal to the electrically conductive tip responsive to a switch position that selectively couples the periodic signal or the electrical resistance-measuring signal to the electrically conductive tip.

According to one embodiment, the method further includes applying an electrode to a second portion of the surface, the electrode being a return signal path for the electrical resistance-measuring signal. The method further includes enabling a gloved tester to facilitate applying the electrical resistance-measuring signal to the surface when the surface is tested. According to one embodiment, the method further includes providing an indicator responsive to a value of electrical resistance measured by the circuit when the surface is tested.

A better understanding of the nature and advantages of the embodiments of the present invention may be gained with reference to the following detailed description and the accompanying drawings.

DETAILED DESCRIPTION

The present invention relates generally to a method and apparatus for testing a patient's skin, and in particular, to testing a patient's skin to find autonomic nervous system sensitivity-points. Auricular acupuncture electrotherapy treatments involve inserting an electrotherapy needle into the skin of a patient at certain sensitivity-points on the ear associated with a particular therapy regimen and applying an electrotherapy signal to the electrotherapy needle. Finding a location to place the needle may be determined by foreknowledge of general locations and testing or measuring local skin resistance. However, electrotherapy treatment acts through the autonomic nervous system so skin resistivity alone may not be the best test indicator for electrotherapy needle placement.

In accordance with one embodiment of the present invention, a test and measurement for electrotherapy needle placement may generate and apply an electrical signal similar or identical to the electrotherapy signal that would be used during treatment to a portion of the patient's skin surface without puncturing the skin. The skin surface is then probed with the electrotherapy signal via an electrically conductive tip, to identify a location that stimulates a vagal response of the patient's autonomic nervous system by monitoring the sympathovagal balance. The identified location may then be pricked by an electrotherapy needle, which is then connected to the electrotherapy signal for a long duration treatment period. Locating the needle sites initially may not constitute therapy but may improve the outcome of planned acupuncture electrotherapy.

Figure 1:
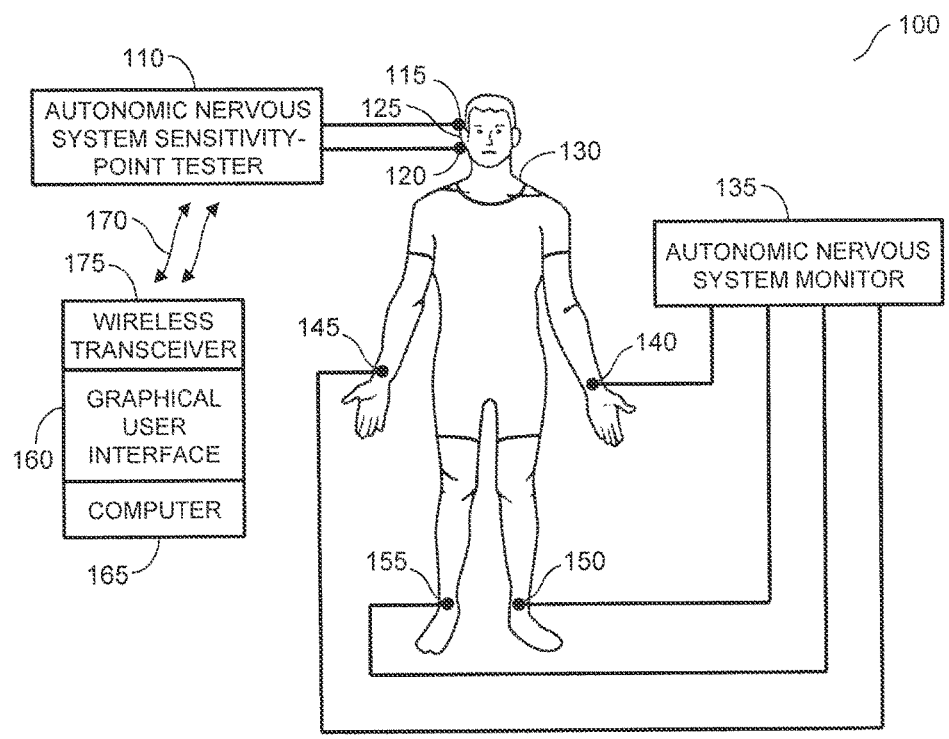
FIG. 1 depicts a simplified block diagram of a patient testing theatre, in accordance with one embodiment of the present invention.

FIG. 1 depicts a simplified block diagram of a patient testing theatre 100, in accordance with one embodiment of the present invention. Patient testing theatre 100 includes an autonomic nervous system sensitivity-point tester 110 coupled to an electrically conductive tip 115 and an electrode 120, which in-turn are connected to an ear 125, hereinafter also referred to as "portion of skin", of a patient 130. In one embodiment, an autonomic nervous system monitor 135 is coupled to electrodes 140, 145, 150, 155 respectively on the patient's left arm, right arm, left leg, right leg to receive quasi-periodical electro cardiogram signals from the cardiac system that are in-turn governed by the patient's autonomic nervous system. The patient is preferably in a supine position on an examination table in a clinical environment for autonomic nervous system testing and monitoring.

In the exemplary embodiment depicted in FIG. 1, the patient is represented as a human. It is understood, however, that the patient may be any living creature possessing an autonomic nervous system and cardiac system. In the exemplary embodiment depicted in FIG. 1, autonomic nervous system sensitivity-point tester 110 is shown as connecting to an ear. It is understood, however, that autonomic nervous system sensitivity-point tester 110 may instead be connected to any portion of skin demonstrated to have nerve connections sensitive enough to affect the autonomic nervous system of the patient.

In one embodiment, the patient testing theatre 100 may include a graphical user interface 160 coupled to a computer 165, which may be coupled via cable (not shown) or via wireless radio transmission 170 to autonomic nervous system sensitivity-point tester 110. Preferably, the autonomic nervous system sensitivity-point tester is a wireless hand held device, which may be programmed or have certain characteristics set by a medical practitioner or technician (not shown) via graphical user interface 160 and computer 165. In one embodiment, computer 165 may be a desktop, laptop, pad, mini-pad, or smart phone that may have a wireless transceiver 175.

The autonomic nervous system monitor 135 is adapted to convert the patient's electro cardiogram signals to, among other information, a sympathovagal balance between the parasympathetic and the sympathetic components of the autonomic nervous system. U.S. Pat. No. 7,092,849 to Lafitte, et al. and co-pending U.S. Pat., titled "STIMULATIVE ELECTROTHERAPY USING AUTONOMIC NERVOUS SYSTEM CONTROL" to Nageshwar, which are incorporated by reference, describe, in part, the theory of operation for autonomic nervous system monitor 135.

Figure 2:
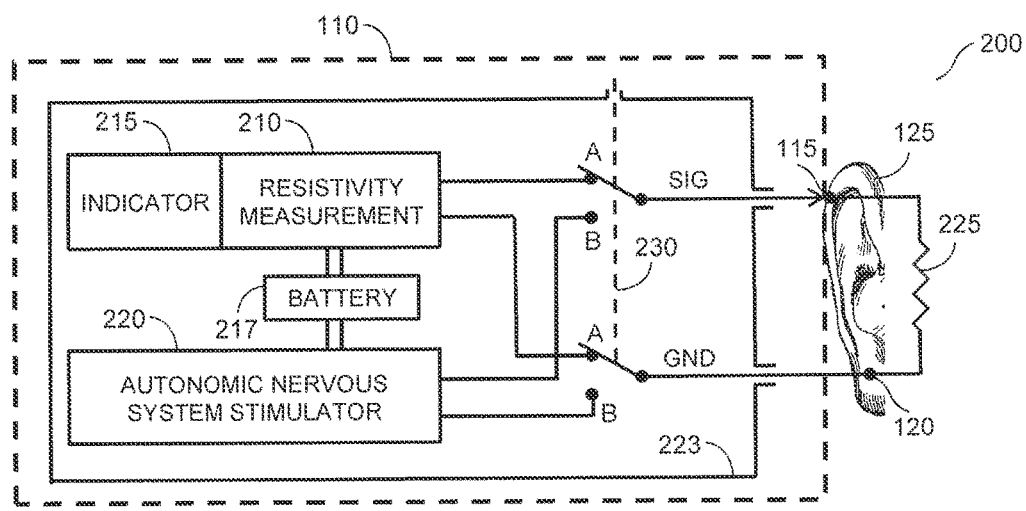
FIG. 2 depicts a simplified block diagram of the autonomic nervous system sensitivity-point tester and the portion of the patient's skin represented in FIG. 1, in accordance with one embodiment of the present invention.

FIG. 2 depicts a simplified block diagram of autonomic nervous system sensitivity-point tester 110 and portion of the patient's skin 125 represented in FIG. 1, in accordance with one embodiment of the present invention. FIG. 2 depicts autonomic nervous system sensitivity-point tester 110, hereinafter also referred to as "circuit", which includes a resistivity measurement unit 210, an indicator 215, an autonomic nervous system stimulator 220, a switch 230, an electrically conductive tip 115, a battery 217, a housing 223, and an electrode 120. Resistivity measurement 210 couples to indicator 215. Battery 217 provides portable power to the circuit and enables hand-held operation.

Resistivity measurement 210 is adapted to generate an electrical resistance-measuring signal to measure a skin resistivity 225 coupled between electrically conductive tip 115 and electrode 120 when the patient is tested. Indicator 215 is responsive to a value of electrical resistance measured by the circuit and may provide a visual indicator, a sonic indicator, and/or a vibrational indicator. For example, indicator 215 may be a buzzer that changes sound pitch in relation to the measured value of skin resistivity 225, which may change as electrically conductive tip 115 is moved around by the medical practitioner to contact different portions of the patient's skin surface.

Autonomic nervous system stimulator 220 is adapted to generate an electrotherapy signal, hereinafter also referred to as "periodic signal" or "periodic signal in time," coupled to electrically conductive tip 115 that stimulates a vagal response of the patient's autonomic nervous system when the patient is tested. Electrically conductive tip 115 provides electrical contact to but does not puncture a portion of the skin surface of the patient when the patient is tested.

Electrode 120 is applied to a different portion of skin than that portion of skin surface being tested to optimize electrotherapy needle placement. Electrode 120 is adapted to be a return signal path, i.e. ground, for either the electrical resistance-measuring signal or the electrotherapy signal thereby enabling a gloved medical practitioner, hereinafter also referred to as "tester" to facilitate applying the electrical resistance-measuring signal or the electrotherapy signal to the patient. Electrode 120 may be a portion of metal foil taped temporarily on the patient's skin or an electrotherapy needle temporarily placed in the patient's skin.

Housing 223 may have an insulating surface and at least one orifice in the insulating surface through which electrically conductive tip 115 protrudes or extends outside the housing. Housing 223 may enclose battery 217 and the circuit. The housing may have a shape that may be adapted to be hand held when the skin surface is tested. In other words, the housing is shaped to fit the hand grasp of a person using autonomic nervous system sensitivity-point tester 110. The insulating surface of the housing may have other orifices for example to allow a tester to operate switch 230 and for electrode 120. Housing 223 may hermetically seal the circuit and seal the orifices, for example using a flexible gasket around the electrically conductive tip to facilitate cleaning and disinfecting autonomic nervous system sensitivity-point tester 110 between testing uses.

Since electrotherapy needle placement punctures the skin, the medical practitioner may be required to wear gloves during needle placement. Prior sensitivity-point tester designs provide the return signal path via the bare hand of the medical practitioner, which must be placed over a metal contact on the housing of the sensitivity-point tester. In contrast, providing electrode 120 is advantageous over prior sensitivity-point tester designs because the medical practitioner's gloves need not be removed in patient testing theatre 100.

Resistivity measurement 210 and autonomic nervous system stimulator 220 are coupled to switch 230, which may be a double-pole, double-throw switch with positions B, A that selectively couple the electrotherapy signal or the electrical resistance-measuring signal respectively to electrically conductive tip 115, while simultaneously coupling the corresponding return signals to electrode 120. Therefore, circuit 110 is in a resistance-measuring mode when switch 230 is in position A and in an autonomic nervous system mode when switch 230 is in position B.

Figure 3:
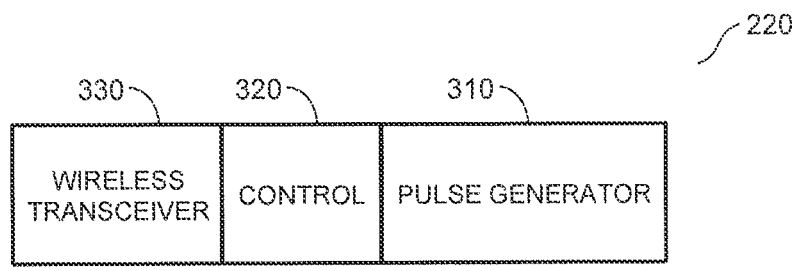
FIG. 3 depicts a simplified block diagram of the autonomic nervous system stimulator represented in FIG. 2, in accordance with one embodiment of the present invention.

FIG. 3 the orifices, for example a simplified block diagram of autonomic nervous system stimulator 220 represented in FIG. 2, in accordance with one embodiment of the present invention. FIG. 3 the orifices, for example autonomic nervous system stimulator 220, which includes a pulse generator 310, a control unit 320, and a wireless transceiver 330. Pulse generator 310 provides the electrotherapy signal, which includes characteristic such as frequency, amplitude, pulse shape, and duty cycle, which are set by control unit 320. The electrotherapy signal may be similar or identical to the signal used during long-term electrotherapy treatment. Control unit 320 couples to wireless transceiver 330, which may receive characteristic settings from computer 165 and set the characteristics in pulse generator 310. Control unit 320 may also perform power saving functions such as turning off either resistivity measurement 210 or autonomic nervous system stimulator 220 responsive to switch 230 position.

Wireless transceiver 330 need not have high bandwidth or long transmission range capability but because autonomic nervous system sensitivity-point tester 110 may be a hand-held portable device, power savings may be desirable to extend battery life. Therefore, wireless transceiver may operate on low bandwidth, power saving radio transmission standards such as Bluetooth®, 6LoWPAN®, ZigBee®, DASH7®, Z-Wave®, MiWi®, or OSION®.

Figure 4A:
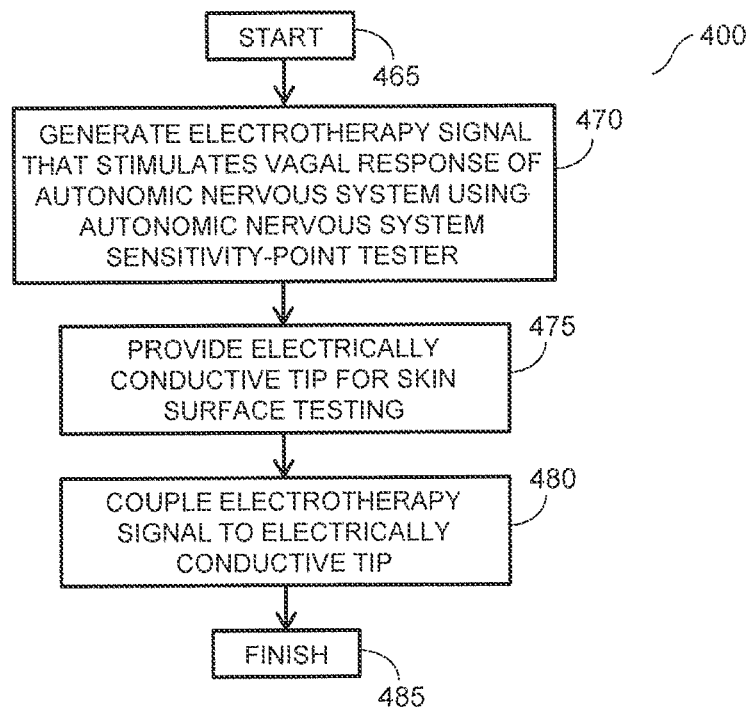
FIG. 4A depicts a simplified flowchart of a method for autonomic nervous system sensitivity-point testing on a skin of a patient, in accordance with one embodiment of the present invention.

FIG. 4A depicts a simplified flowchart of a method 400 for autonomic nervous system sensitivity-point testing on a skin of a patient, in accordance with one embodiment of the present invention. Referring simultaneously to FIG. 2 and FIG. 4A, the method starts 465 by the medical practitioner generating 470 the electrotherapy signal that stimulates a vagal response of an autonomic nervous system of the patient when the patient is tested by using autonomic nervous system sensitivity-point tester 110 in autonomic nervous system mode, i.e. setting switch 230 in position B. The electrically conductive tip 115 is provided 475 that electrically contacts but does not puncture the skin surface when the patient is tested. Setting switch 230 in position B couples 480 the electrotherapy signal to electrically conductive tip 115, as described above. Thus, before finish 485 of this embodiment, the autonomic nervous system sensitivity-point tester 110 is set up to do skin surface testing on the patient.

Figure 4B:
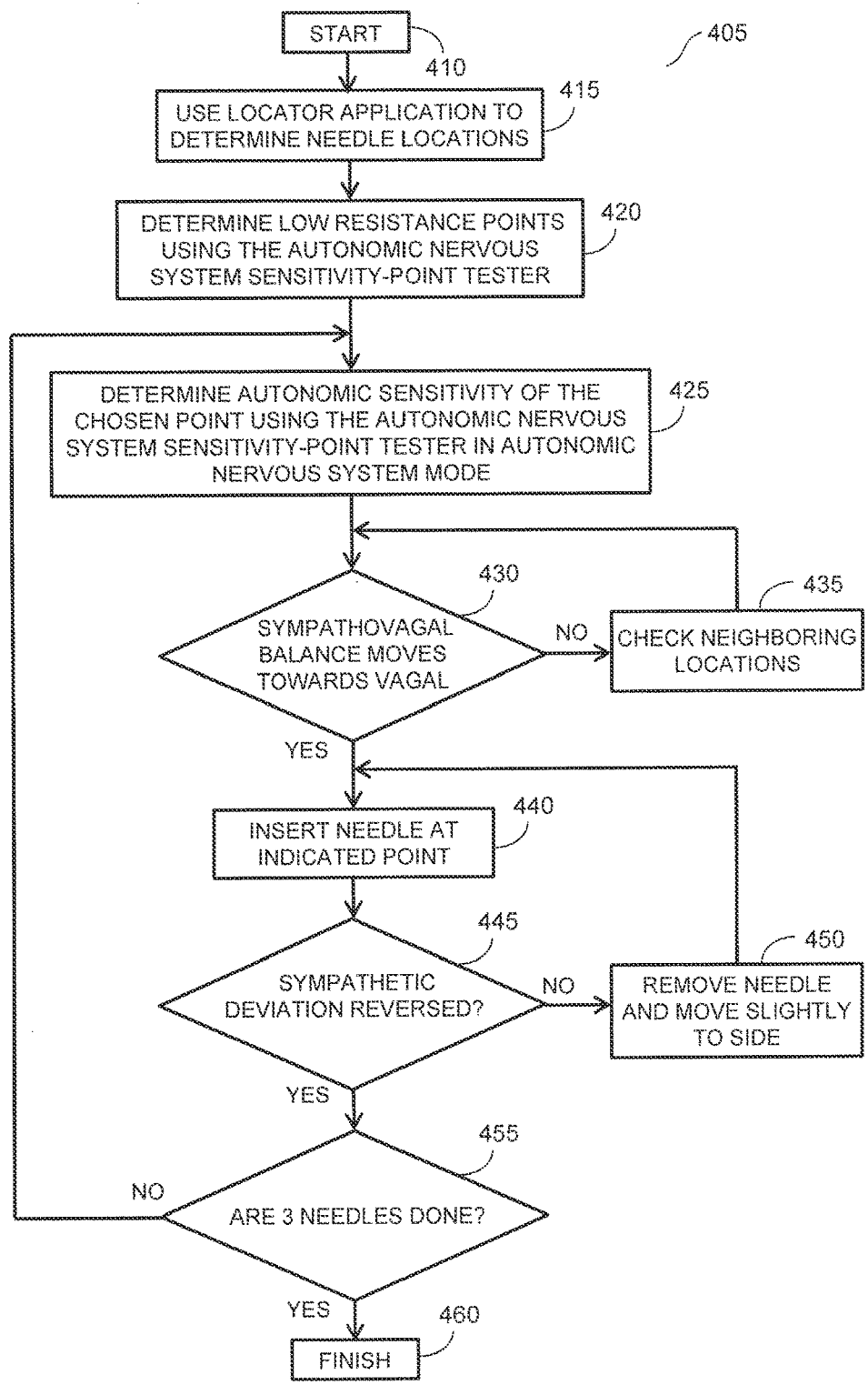
FIG. 4B depicts a simplified flowchart of a method for autonomic nervous system sensitivity-point testing on a skin of a patient, in accordance with another embodiment of the present invention.

FIG. 4B depicts a simplified flowchart of a method 405 for autonomic nervous system sensitivity-point testing on a skin of a patient, in accordance with another embodiment of the present invention. Referring simultaneously to FIG. 1 and FIG. 4B, the method starts 410 in one embodiment, by using 415 a locator application running on computer 165 to generally determine the needle locations. In other words, choosing a first portion of the patient's skin is done by obtaining a preliminary skin location, e.g. on the ear, from graphical user interface 160 coupled to computer 165 executing a program responsive to a symptom of the patient. For example, the patient may be complaining to the medical practitioner of a pain in the lower back. The medical practitioner may select that symptom on graphical user interface 160, which responds by displaying the general location on a map of the ear, where acupuncture electrotherapy has been associated with lower back pain treatment.

Referring simultaneously to FIG. 2 and FIG. 4B, the sensitivity-point location may be further localized by choosing a first portion of skin within the region identified in step 415 by determining 420 low resistance points using autonomic nervous system sensitivity-point tester 110 operating in resistance-measuring mode, i.e. by setting switch 230 in position A. Then resistivity measurement 210 generates the electrical resistance-measuring signal, which is coupled to electrically conductive tip 115. Electrode 120 is applied to a second portion of skin, the electrode being a return signal path for the resistance-measuring signal The medical practitioner may then apply the electrical resistance-measuring signal to the first portion of skin with electrically conductive tip 115 that electrically contacts but does not puncture the skin when the patient is tested. The electrical resistance at the first portion of skin is measured by resistivity measurement 210 and causes indicator 215 to provide an indication responsive to a value of skin resistivity 225, i.e. changing an emitted sound pitch correlated with the value. The medical practitioner moves or probes the electrically conductive tip on the skin surface in response to the indication to selectively find a low resistance location of skin near the first portion of skin.

The medical practitioner may then further optimize the electrotherapy needle insertion location by determining 425 the autonomic sensitivity of the chosen point using autonomic nervous system sensitivity-point tester 110 in autonomic nervous system mode, i.e. by setting switch 230 in position B. Then autonomic nervous system stimulator 220 generates the electrotherapy signal, which is coupled to electrically conductive tip 115. Electrode 120 is applied, if not already applied during step 420, to another portion of skin, the electrode being a return signal path for the electrotherapy signal.

The medical practitioner may then apply the electrotherapy signal to the selected portion of skin with electrically conductive tip 115 that electrically contacts but does not puncture the skin when the patient is tested. The electrotherapy signal may stimulate a vagal response of the autonomic nervous system of the patient when electrically conductive tip 115 is located in contact with an autonomic nervous system sensitivity-point on the skin surface when the patient is tested. Referring simultaneously to FIG. 1 and FIG. 4B, to measure the autonomic nervous system, the medical practitioner couples autonomic nervous system monitor 135 to the patient as described above. Autonomic nervous system monitor 135 analyzes a state of the autonomic nervous system of the patient from a time-varying signal representing a chaotic series of time intervals between quasi-periodical events produced by a cardiac system of the patient, i.e. from the patient's electrocardiogram. Autonomic nervous system monitor 135 also measures and displays a first sympathovagal balance of the patient.

Figure 5:
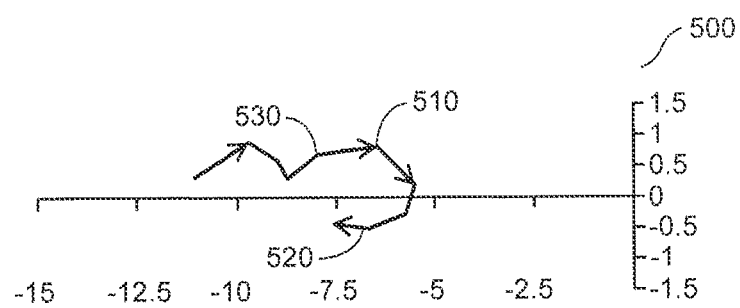
FIG. 5 depicts an exemplary response of a sympathovagal balance used in the method represented in FIG. 4B.

FIG. 5 depicts an exemplary response of a sympathovagal balance 500 used in method 425 represented in FIG. 4B. FIG. 5 depicts sympathovagal balance 500, which plots balance trajectory 530 for the patient in real time as shown by the series of arrows on the balance trajectory. The horizontal axis represents a parasympathetic or vagal response in the direction towards higher negative numbers, i.e. towards the left direction on the plot. Conversely, a sympathetic response is represented on the plot's horizontal axis in the direction of smaller negative numbers, i.e. towards the right of the plot. A sympathetic trending balance trajectory 530 over time indicates increasing pain or dysfunction, while a vagal trending balance trajectory indicates pain relief. In this example, the patient may be suffering anxiety to the clinical setting and the patient's balance trajectory 530 starts out generally moving away from the parasympathetic or vagal part of the horizontal axis and towards the sympathetic direction as indicated at point 510.

Referring simultaneously to FIG. 4B and FIG. 5, the medical practitioner determines 430 a response outcome based on the sympathovagal balance. The response outcome is positive when the sympathovagal balance moves towards the vagal response as shown at point 520 indicating the electrically conductive tip 115 is positioned optimally on the skin surface and the patient's autonomic nervous system is responding favorably to the electrotherapy signal. In contrast, the response outcome is negative when the sympathovagal balance does not move towards the vagal response.

When the response outcome is negative, the medical practitioner checks 435 or chooses a slightly different neighboring portion of skin of the patient abutting the earlier portion of chosen skin. The medical practitioner repeats applying the electrotherapy signal, measuring the sympathovagal balance, and determining the response outcome until the response outcome is positive or until a certain predetermined number of portions of skin are tested or time has elapsed.

When the response outcome is positive, the medical practitioner inserts 440 an electrotherapy needle at that portion of skin. The electrotherapy needle location selected with the procedure described above has been tested earlier at step 430 raising the confidence that the same electrotherapy signal applied to that location during the treatment regimen should have the desired beneficial effect on the patient's autonomic nervous system.

The needle insertion will cause a little pain creating a sympathetic deviation such as shown at point 510 on balance trajectory 530 that should quickly subside or reverse. However, the needle insertion location may be at a point that will stimulate an undesired long-term pain response. Therefore, after needle insertion, the medical practitioner measures a second sympathovagal balance of the patient to determine 445 a sympathetic deviation reversal outcome based on the second sympathovagal balance. The reversal outcome is positive when the second sympathovagal balance reverses from a sympathetic response towards a vagal response as shown at point 520 on balance trajectory 530. The reversal outcome is negative when the second sympathovagal balance does not reverse from a sympathetic response towards a vagal response.

When the reversal outcome is negative, the medical practitioner removes 450 the electrotherapy needle from the portion of skin and moves the needle slightly to the side to choose another portion of skin abutting the earlier portion of skin. The medical practitioner repeats inserting, measuring the second sympathovagal balance, and determining the reversal outcome until the reversal outcome is positive or until a certain predetermined number of portions of skin are tested or time has elapsed.

The electrotherapy treatment may require more than one stimulation point on the patient's ear. For example, one point may be stimulated to address lower back pain and another point may be stimulated for general pain relief. Accordingly, when the reversal outcome at step 445 is positive, the medical practitioner determines 455 a number of inserted electrotherapy needles. The testing is finished 460 when the number of inserted electrotherapy needles is equal to a predetermined number of electrotherapy needles required for the electrotherapy treatment, e.g. three stimulation needles—one needle located for a specific symptom and two needles located at two different locations for general pain relief. When a number of inserted electrotherapy needles is less than the predetermined number of electrotherapy needles, the medical practitioner repeats choosing the location, applying the electrotherapy signal, measuring the first sympathovagal balance, determining the response outcome, inserting the needle, measuring the second sympathovagal balance, and determining the reversal outcome.

The above embodiments of the present invention are illustrative and not limiting. Various alternatives and equivalents are possible. Although, the invention has been described with reference to a human patient by way of an example, it is understood that the invention is not limited by the type of patient so long as the patient has an autonomic nervous system and cardiac system. Although, the invention has been described with reference to auricular acupuncture electrotherapy by way of an example, it is understood that the invention is not limited by the location of the skin portion being tested so long as the location has autonomic nervous system sensitivity-points. Other additions, subtractions, or modifications are obvious in view of the present disclosure and are intended to fall within the scope of the appended claims.

What is claimed is:

1. A method for autonomic nervous system sensitivity-point testing on a skin of a patient, the method comprising:
    generating an electrotherapy signal that stimulates a vagal response of an autonomic nervous system of the patient when the patient is tested;
    providing an electrically conductive tip that electrically contacts but does not puncture the skin when the patient is tested;
    coupling the electrotherapy signal to the electrically conductive tip;
    applying the electrotherapy signal to a first portion of the skin with the electrically conductive tip;
    applying an electrode to a second portion of the skin, the electrode providing a return signal path for the electrotherapy signal;
    measuring a first sympathovagal balance of the patient based on the electrotherapy signal passed through the electrically conductive tip and the electrode, wherein the first sympathovagal balance of the patient is associated with an arrow on a balance trajectory; wherein the balance trajectory projecting on an abscissa running from smaller numbers to larger numbers such that movement of the balance trajectory toward the smaller numbers along the abscissa corresponds to the vagal response, while movement of the balance trajectory toward the larger numbers along the abscissa corresponds to a sympathetic response; and
    determining a response outcome based on the arrow on the balance trajectory of the patient, wherein the response outcome indicates that the first portion of the skin is suitable for electrotherapy when the arrow of the first sympathovagal balance moves towards the smaller numbers along the abscissa when the electrotherapy signal is passed through the patient, and wherein the response outcome indicates that the first portion of the skin is unsuitable for the electrotherapy when the arrow of the first sympathovagal balance does not move towards smaller numbers along the abscissa, when the electrotherapy signal is passed through the patient.

2. The method of claim 1 wherein generating the electrotherapy signal includes wirelessly setting a characteristic of the electrotherapy signal.

3. The method of claim 2 wherein the characteristic is selected from the group consisting of a frequency, an amplitude, a pulse shape, and a duty cycle.

4. The method of claim 1, wherein providing an electrically conductive tip further comprising:
    generating an electrical resistance-measuring signal; and
    coupling the electrical resistance-measuring signal to the electrically conductive tip.

5. The method of claim 1 further comprising:
    choosing the first portion of the skin of the patient.

6. The method of claim 5 further comprising:
    choosing a third portion of the skin of the patient abutting the first portion of the skin when the response outcome indicates that the first portion of the skin is unsuitable for the electrotherapy; and
    applying the electrotherapy signal to the third portion of the skin; and
    measuring the first sympathovagal balance with the electrotherapy signal applied to the third portion of the skin.

7. The method of claim 5 wherein choosing the first portion of the skin includes obtaining a preliminary location of the first portion of the skin from a graphical user interface coupled to a computer executing a program responsive to a symptom of the patient.

8. The method of claim 5 wherein the first portion of the skin is located on an ear of the patient.

9. The method of claim 5 wherein the electrode providing the return signal path for the electrotherapy signal thereby enables a gloved medical practitioner to facilitate applying the electrotherapy signal.

10. The method of claim 5 wherein measuring the first sympathovagal balance includes:
    coupling an autonomic nervous system monitor to the patient; and
    analyzing a state of the autonomic nervous system of the patient from a time-varying signal representing a chaotic series of time intervals between quasi-periodical events produced by a cardiac system of the patient.

11. The method of claim 5 further comprising inserting an electrotherapy needle at the first portion of the skin when the response outcome indicates that the first portion of the skin is suitable for the electrotherapy.

12. The method of claim 11, further comprising:
    measuring after inserting the electrotherapy needle at the first portion of the skin, a second sympathovagal balance of the patient, wherein the second sympathovagal balance of the patient is associated with a second arrow on the balance trajectory; and
    determining a reversal outcome based on the second arrow on the second sympathovagal balance;

wherein the reversal outcome equates to a larger number of the abscissa of the balance trajectory than obtained on the first sympathovagal balance, when the second sympathovagal balance reverses in comparison to the first sympathovagal balance; and wherein the reversal outcome equates to a smaller number of the abscissa of the balance trajectory than obtained on the first sympathovagal balance, when the second sympathovagal balance does not reverse in comparison to the first sympathovagal balance.

13. The method of claim 12 further comprising:

removing the electrotherapy needle from the first portion of the skin, wherein the reversal outcome is an arrow pointing to a negative direction on the abscissa, wherein the negative direction points to negative numbers;

choosing a third portion of the skin of the patient abutting the first portion of the skin;

inserting the electrotherapy needle at the third portion of the skin; and measuring the second sympathovagal balance with the electrotherapy needle at the third portion of the skin.

14. The method of claim 12, further comprising:

determining a number of inserted electrotherapy needles when the reversal outcome equates to the larger number of the abscissa of the balance trajectory; and finishing the testing when the number of inserted electrotherapy needles is equal to a predetermined number of electrotherapy needles.

15. The method of claim 14, wherein the predetermined number of electrotherapy needles is equal to three.

16. The method of claim 5, further comprising:

generating an electrical resistance-measuring signal;

coupling the electrical resistance-measuring signal to the electrically conductive tip;

applying the electrical resistance-measuring signal to a first tested portion of the skin with the electrically conductive tip;

measuring an electrical resistance at the first tested portion of the skin;

providing an indication responsive to a value of the electrical resistance;

iteratively moving the electrically conductive tip in response to the indication to selectively find an optimal location of the skin in a vicinity of the first tested portion of the skin, wherein the location has a lower resistance than the resistance at the first tested portion of the skin; and choosing the first portion of the skin as the location having a lower resistance.

17. The method of claim 16 wherein applying the resistance-measuring signal includes applying the electrode to a third portion of the skin, the electrode being a return signal path for the resistance-measuring signal.

18. The method of claim 16 wherein applying the electrotherapy signal includes switching an electrical probe including the electrically conductive tip and the electrode from a resistance-measuring mode to an autonomic nervous system mode.

19. The method of claim 1, wherein the vagal response is a response toward pain relief.

20. The method of claim 1, wherein the sympathetic response is a response toward more pain.

21. An electrical system for autonomic nervous system sensitivity-point testing on a skin of a patient, the electrical system comprising:

a stimulator apparatus, including:

a circuit configured to generate an electrotherapy signal that stimulates a response of an autonomic nervous system of the patient when the patient is tested;

an electrically conductive tip configured to electrically contact but not puncture a first portion of the skin when the patient is tested, wherein the electrotherapy signal is coupled to the electrically conductive tip; and an electrode configured to be applied to a second portion of the skin, the electrode configured to provide a return signal path for the electrotherapy signal to facilitate measurement of a first sympathovagal balance of the patient based on the electrotherapy signal passed through the electrically conductive tip and the electrode; and a computing apparatus, including processing circuitry configured to:

measure the first sympathovagal balance of the patient based on the electrotherapy signal passed through the electrically conductive tip and the electrode, wherein the first sympathovagal balance of the patient is associated with an arrow on a balance trajectory, the balance trajectory projecting on an abscissa running from smaller numbers to larger numbers such that movement of the balance trajectory toward the smaller numbers along the abscissa corresponds to a vagal response, while movement of the balance trajectory toward the larger numbers along the abscissa corresponds to a sympathetic response; and determining a response outcome based on the arrow on the balance trajectory of the patient, wherein the response outcome indicates that the first portion of the skin is suitable for electrotherapy when the arrow of the first sympathovagal balance moves towards the smaller numbers along the abscissa when the electrotherapy signal is passed through the patient, and wherein the response outcome indicates that the first portion of the skin is unsuitable for the electrotherapy when the arrow of the first sympathovagal balance does not move towards the smaller numbers along the abscissa, when the electrotherapy signal is passed through the patient.

22. The electrical system of claim 21 wherein the electrode being configured to provide the return signal path for the electrotherapy signal thereby enables a gloved medical practitioner to facilitate applying the electrotherapy signal to the patient.

23. The electrical system of claim 21 wherein the circuit includes:

a wireless radio transceiver; and a control circuit adapted to set a characteristic of the electrotherapy signal, the characteristic received by an input of the wireless transceiver.

24. The electrical system of claim 23 wherein the wireless radio transceiver operates on a transmission standard.

25. The electrical system of claim 23 wherein the characteristic is selected from the group consisting of a frequency, an amplitude, a pulse shape, and a duty cycle.

26. The electrical system of claim 21 wherein the circuit is further adapted to generate an electrical resistance-measuring signal, wherein the electrical resistance-measuring signal is coupled to the electrically conductive tip responsive to a switch position that selectively couples the electrotherapy signal or the electrical resistance-measuring signal to the electrically conductive tip.

27. The electrical system of claim 26 wherein the electrode is further configured to provide a return signal path for the electrical resistance-measuring signal.

28. The electrical system of claim 26 further comprising an indicator responsive to a value of electrical resistance measured by the circuit.

29. The electrical system of claim 28 wherein the indicator is selected from the group consisting of a visual indicator, a sonic indicator, and a vibrational indicator.

30. An electrical testing system, comprising:
a stimulator apparatus, including:
a battery;
a circuit configured to generate a periodic signal in time;
an electrically conductive tip configured to electrically contact but not puncture a first portion of a surface when the surface is tested, wherein the periodic signal is coupled to the electrically conductive tip;
an electrode configured to be applied to a second portion of the surface, the electrode being configured to provide a return signal path for the periodic signal to facilitate measurement of a first sympathovagal balance of a patient based on the periodic signal passed through the electrically conductive tip and the electrode; and
a computing apparatus, including processing circuitry configured to:
measure the first sympathovagal balance of the patient based on the periodic signal passed through the electrically conductive tip and the electrode, wherein the first sympathovagal balance of the patient is associated with an arrow on a balance trajectory; the balance trajectory projecting on an abscissa running from smaller numbers to larger numbers such that movement of the balance trajectory toward the smaller numbers along the abscissa corresponds to a vagal response, while movement of the balance trajectory toward the larger numbers along the abscissa corresponds to a sympathetic response; and
determine a response outcome based on the arrow on the balance trajectory of the patient, wherein the response outcome indicates that the first portion of the surface is suitable for electrotherapy when the arrow of the first sympathovagal balance moves towards smaller-numbers along the abscissa when the periodic signal is passed through the patient, and wherein the response outcome indicates that the first portion of the surface is unsuitable for the electrotherapy when the arrow of the first sympathovagal balance does not move toward the smaller numbers along the abscissa, when the periodic signal is passed through the patient.

31. The electrical testing system of claim 30 wherein the electrode being configured to provide the return signal path for the periodic signal thereby enables a gloved tester to facilitate applying the periodic signal to the first portion of the surface when the surface is tested.

32. The electrical testing system of claim 30, wherein the stimulator apparatus further includes a housing having an insulating surface and at least a first orifice in the insulating surface, the electrically conductive tip adapted to protrude outside the housing through the first orifice, the housing enclosing the battery and the circuit, the housing having a shape being adapted to be handheld when the surface is tested.

33. The electrical testing system of claim 32, wherein the housing is adapted to hermetically seal the stimulator apparatus.

34. The electrical testing system of claim 30 wherein the circuit includes:
a wireless radio transceiver; and
a control circuit adapted to set a characteristic of the periodic signal, the characteristic received by an input of the wireless transceiver.

35. The electrical testing system of claim 34 wherein the wireless radio transceiver operates on a transmission standard.

36. The electrical testing system of claim 34 wherein the characteristic is selected from the group consisting of a frequency, an amplitude, a pulse shape, and a duty cycle.

37. The electrical testing system of claim 30 wherein the circuit is further adapted to generate an electrical resistance-measuring signal, wherein the electrical resistance-measuring signal is coupled to the electrically conductive tip responsive to a switch position that selectively couples the periodic signal or the electrical resistance-measuring signal to the electrically conductive tip.

38. The electrical testing system of claim 37 wherein the electrode is further configured to provide a return signal path for the electrical resistance-measuring signal.

39. The electrical testing system of claim 37, wherein the stimulator apparatus further includes an indicator responsive to a value of electrical resistance measured by the circuit.

40. The electrical testing system of claim 39 wherein the indicator is selected from the group consisting of a visual indicator, a sonic indicator, and a vibrational indicator.

41. A method for electrical testing comprising:
providing a battery;
generating a periodic signal in time from a circuit;
providing an electrically conductive tip adapted to electrically contact but not puncture a first portion of a skin when the skin is tested;
coupling the periodic signal to the electrically conductive tip;
applying an electrode to a second portion of the skin, the electrode being a return signal path for the periodic signal;
measuring a first sympathovagal balance of the patient based on the periodic signal passed through the electrically conductive tip and the electrode, wherein the first sympathovagal balance of the patient is associated with an arrow on a balance trajectory; the balance trajectory projecting on an abscissa running from smaller numbers to larger numbers such that movement of the balance trajectory toward the smaller numbers along the abscissa corresponds to a vagal response, while movement of the balance trajectory toward the larger numbers along the abscissa corresponds to a sympathetic response; and
determine a response outcome based on the arrow on the balance trajectory of the patient, wherein the response outcome indicates that the first portion of the skin is suitable for electrotherapy when the arrow of the first sympathovagal balance moves towards the smaller-numbers along the abscissa when the periodic signal is passed through the patient, and wherein the response outcome indicates that the first portion of the skin is unsuitable for the electrotherapy when the arrow of the first sympathovagal balance does not move toward the smaller numbers along the abscissa when the periodic signal is passed through the patient.

42. The method of claim 41, wherein the electrode being the return signal path for the periodic signal thereby enables a gloved tester to facilitate applying the periodic signal to the first portion of the skin when the first portion of the skin is tested.

43. The method of claim 41, further comprising:
providing a housing having an insulating surface and at least a first orifice in the insulating surface;
protruding the electrically conductive tip outside the housing through the first orifice;
enclosing the battery and the circuit with the housing; and
shaping the housing to be handheld when the skin is tested.

44. The method of claim 43, further comprising hermetically sealing the housing.

45. The method of claim 41, further comprising:
providing a wireless radio transceiver;
setting a characteristic of the periodic signal via the circuit; and
receiving the characteristic by an input of the wireless transceiver.

46. The method of claim 45, wherein the wireless radio transceiver operates on a transmission standard.

47. The method of claim 45, wherein the characteristic is selected from the group consisting of a frequency, an amplitude, a pulse shape, and a duty cycle.

48. The method of claim 41, further comprising:
generating an electrical resistance-measuring signal by the circuit; and
coupling the electrical resistance-measuring signal to the electrically conductive tip responsive to a switch position that selectively couples the periodic signal or the electrical resistance-measuring signal to the electrically conductive tip.

49. The method of claim 48, wherein the electrode is further configured to provide a return signal path for the electrical resistance-measuring signal.

50. The method of claim 48, further comprising:
providing an indicator responsive to a value of electrical resistance measured by the circuit when the skin is tested.

51. The method of claim 50 wherein the indicator is selected from the group consisting of a visual indicator, a sonic indicator, and a vibrational indicator.

* * * * *